United States Patent [19]
Zaffaroni

[11] 3,971,367
[45] July 27, 1976

[54] INTRAUTERINE DEVICE HAVING MEANS FOR CHANGING FROM UTERINE-RETENTIVE SHAPE TO NONUTERINE-RETENTIVE SHAPE

[75] Inventor: Alejandro Zaffaroni, Atherton, Calif.

[73] Assignee: Alza Corporation, Palo Alto, Calif.

[22] Filed: June 4, 1975

[21] Appl. No.: 583,829

Related U.S. Application Data

[63] Continuation-in-part of Ser. No. 319,014, Dec. 27, 1972, Pat. No. 3,898,986.

[52] U.S. Cl. ............................... 128/130; 128/260
[51] Int. Cl.² .......................................... A61F 5/46
[58] Field of Search ...................... 128/127–130, 128/260; 424/19, 14, 21, 22, 33, 37

[56] References Cited
UNITED STATES PATENTS

| | | | |
|---|---|---|---|
| 3,143,472 | 8/1964 | Lappes | 424/33 |
| 3,533,406 | 10/1970 | Tatum | 128/130 |
| 3,625,214 | 12/1971 | Higuchi | 128/260 |
| 3,636,956 | 1/1972 | Schneider | 128/335.5 |
| 3,640,741 | 2/1972 | Etes | 434/32 |
| 3,659,596 | 5/1972 | Robinson | 128/130 |
| 3,699,951 | 10/1972 | Zaffaroni | 128/130 |
| 3,710,795 | 1/1973 | Higuchi | 128/130 |

*Primary Examiner*—Lawrence W. Trapp
*Attorney, Agent, or Firm*—Paul L. Sabatine; Edward L. Mandell; Thomas E. Ciotti

[57] ABSTRACT

An improved intrauterine device which delivers a predetermined therapeutically effective dosage of drug locally to the uterus over a defined period of time is disclosed. The device is initially of a uterine-retentive shape. The device is characterized by undergoing a structural biotransformation in the uterus such that at the completion of the defined period of drug delivery it has achieved a nonuterine-retentive configuration.

23 Claims, 7 Drawing Figures

INTRAUTERINE DEVICE HAVING MEANS FOR CHANGING FROM UTERINE-RETENTIVE SHAPE TO NONUTERINE-RETENTIVE SHAPE

CROSS-REFERENCE TO RELATED APPLICATION

This application is a continuation-in-part of U.S. Patent application Ser. No. 319,014 filed on Dec. 27, 1972, now U.S. Pat. No. 3,898,986. This application is assigned to the same assignee as Ser. No. 319,014 and benefit of its filing date is claimed.

BACKGROUND OF THE INVENTION

1. Field of the Invention

This invention relates to an improved drug dispensing intrauterine device. In a preferred embodiment this invention concerns an improved intrauterine device for dispensing locally to the uterus an interceptive agent for terminating pregnancy.

2. The Prior Art

Presently, a critical need exists for an acceptable means for the direct continuous delivery of drugs directly (locally) to the uterus. In the prior art, it is most common to administer drugs to the uterus systemically, such as by injection, by ingestion or by intravenous infusion. With systemic administration, the amount of drugs needed to achieve the desired uterine purpose is so large that serious undesirable side effects often occur in many body organs.

Vaginal suppositories are another prior art drug form which has been used to administer drugs to the uterus, since some of the vaginally-administered drug which is absorbed through the vaginal walls passes via the circulatory system to the uterus. This method of delivery is essentially systemic and thus leads to the same serious side effects.

In my earlier patent applications U.S. Ser. No. 185,208 now U.S. Pat. No. 3,896,819, filed Sept. 30, 1971, and U.S. Ser. No. 281,445 filed Aug. 17, 1972, now U.S. Pat. No. 3,845,761, I disclose intrauterine devices which contain drugs and which administer a controlled flow of these drugs locally to the uterus. Such devices deliver drugs locally to the uterus only for a finite period of time and then must be removed either because the need for medication has passed or because the supply of drug in the device is exhausted and a new device is required. With conventional devices this removal is a major problem. The uterus is lined with an extremely delicate vessel-rich and gland-rich tissue, the endometrium, which surrounds and intimately contacts any object placed within it. Any probing for or the twisting and manipulating of an intrauterine device to effect its removal will almost certainly gouge and disrupt (or very likely damage) the endometrium and the vessels and glands it contains. Also, the geometry of the uterine cavity and cervix poses further complications as the cervix, through which any device must be removed, is relatively inaccessible and substantially smaller in diameter than the uterus. For these reasons, the removal of intrauterine devices is now almost always carried out by skilled medical personnel.

Attempts to make intrauterine devices in a shape or size which is easier to remove often introduces further complications since easy removal is, almost by definition, antagonistic to an acceptable degree of uterine retention. A high degree of uterine retention is critical to the success of a drug dispensing intrauterine device. Premature expulsion of the device by the uterus is highly undesirable as it results in the premature termination of drug administration. To give the desired therapy, the device must be retained in the uterus for the entire period planned. A device which is easily inserted and removed is also easily expelled. Conversely, a device having good retention characteristics is difficult to insert or remove without damage.

Insertion has been facilitated in the prior art by forming a uterine-retentive shaped device from metal or plastic having an elastic memory, deforming the device by placing it in a narrow straight flexible insertion tube, guiding one end of the tube to and through the cervix, and extruding the device out of the insertion tube into the uterus where, as a result of its elastic memory, it assumes its uterine retentive shape. While this method promotes an otherwise difficult insertion, it is not effective to effect removal, as the manipulation needed to introduce an intrauterine device into an "insertion" tube for removal is at least as harmful to the uterine tissues as the removal itself would be.

OBJECTS OF THE INVENTION

Accordingly, it is a primary object of this invention to provide an improved drug dispensing intrauterine device.

A more particular object of this invention is to provide an improved drug dispensing intrauterine device which does not pose the problems associated with removal from the uterus after completion of the therapeutic program.

Yet another object of this invention is to provide a drug-dispensing intrauterine device which delivers drugs to the uterus with increased therapeutic efficiency.

STATEMENT OF THE INVENTION

To accomplish these and other objectives, the present invention provides an intrauterine device which releases a therapeutically effective flow of drug to the uterus over a defined dosage period. The device of this invention is fabricated to undergo a structural biotransformation during its period in the uterus, from an initial uterine-retentive configuration to a configuration at the completion of the defined dosage period which is not uterine-retentive and which permits the device to be facilely manually removed or to be spontaneously eliminated from the uterus.

While the invention encompasses delivery of drugs, broadly, over a wide range of time period, in a preferred embodiment, the devices of this invention are employed to release an interceptive agent for pregnancy termination locally to the uterus over a therapeutically effective defined period of time on the order of from about 8 hours to about 72 hours. At the completion of this period of time, the device has undergone biotransformation and is easily removed or spontaneously eliminated from the uterus.

DETAILED DESCRIPTION OF THE INVENTION

Brief Description of the Drawings

The invention will be described with reference to the drawings wherein.

Definition of Terms

Devices of this invention initially upon insertion in the uterus are of a uterine-retentive configuration. The term "uterine-retentive" as used in the specification and claims is defined as the property or characteristic of a shape to not be susceptible to expulsion by the uterus, even when the uterus is undergoing uterine contraction and the like.

Devices of this invention undergo a structural biotransformation. The term "structural biotransformation" as used herein is defined as a change which takes place in cavity from a solid frame of an intrauterine device in response to the environment of the uterus wherein the frame innocuously disintegrates, breaks down, or collapses from an initial unit structure or entity to a second structure, or structures, or particles, having a different form than the initial unit structure. Structural biotransformation can proceed through physical or chemical degradative processes, for example, deflation; a loss of rigor of a structural member; or dissolution or erosion of a structural member by solubilization, oxidation or reduction, enzymatic action, hydrolysis, ionization or ion exchange. Devices of this invention release drugs to the uterus. In a preferred embodiment, they release interceptive agents. The term "interceptive agents" as used herein refers to those agents or drugs which treat the tissue components of the uterus itself and/or the fertilized egg or embryo at various stages of its development to bring about or facilitate a termination of pregnancy such as by promoting expulsion or absorption of the embryo.

Detailed Description of the Drawings

Figure 1:
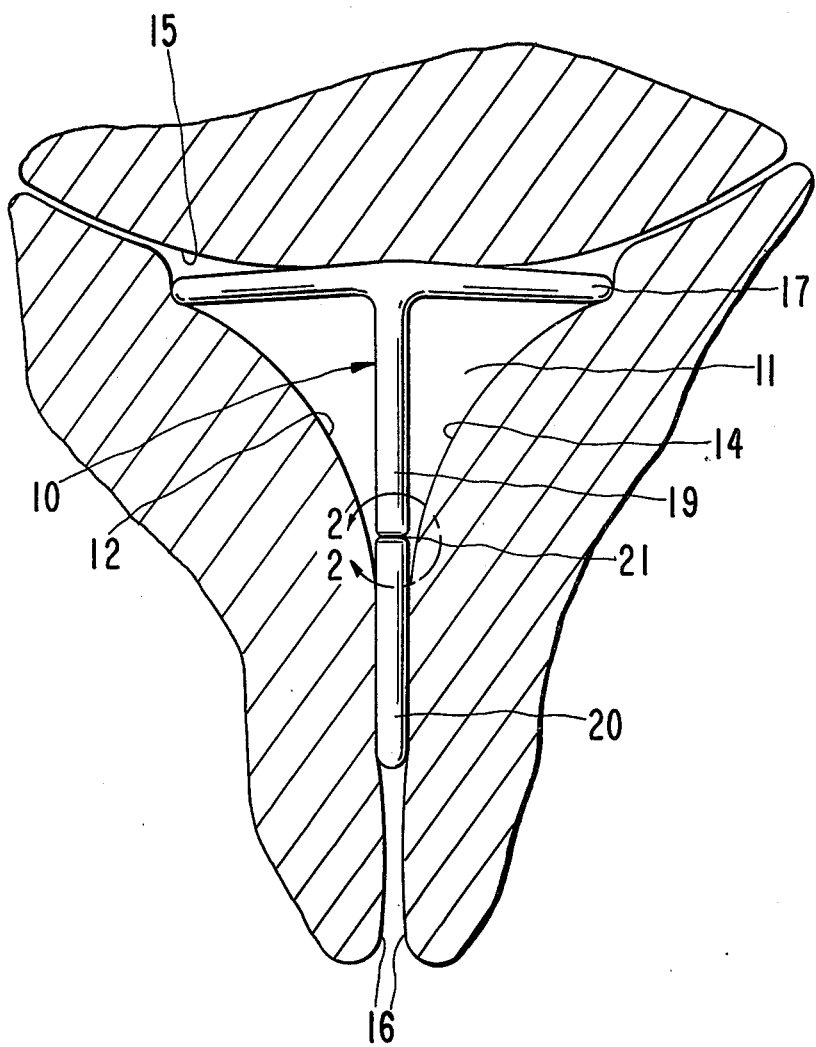
FIG. 1 is a cross-sectional elevational view of a uterus containing a drug-dispensing intrauterine device of this invention.
Figure 2:
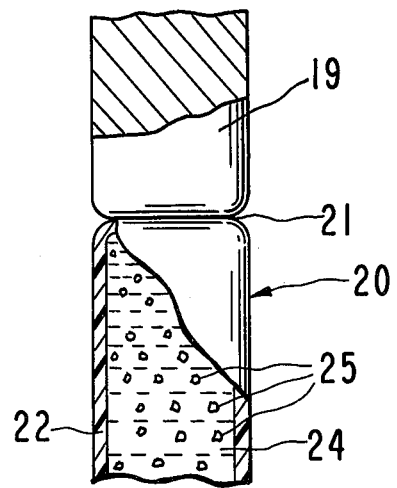
FIG. 2 is an enlarged cutaway section of the device shown in FIG. 1.

Referring to the drawings and particularly to FIGS. 1 and 2, in FIG. 1 a drug-releasing intrauterine device 10 is depicted lodged in uterus 11 defined by walls 12 and 14 and fundus uteri 15 and terminating at cervix uteri 16. Walls 12 and 14 and fundus uteri are comprised of endometrium, a soft, tender, easily-disturbed tissue. Device 10 comprises cross bar 17 and axial rod 19. As detailed in FIG. 2, drug dispenser 20 is attached by adhesive 21 to axial rod 19 at a position distal to cross bar 17. Drug dispenser 20 comprises a drug-permeable wall 22 surrounding a reservoir of drug carrier 24 and drug 25. Dispenser 20, as shown, passes drug by a diffusion control mechanism, that is, drug diffuses through wall 22 to be released and wall 22 is a rate release controlling material. Drug dispenser 20 is depicted in FIG. 2 with carrier 24 a liquid and with drug present in excess of its solubility limit in the liquid carrier. Such a diffusion drug dispenser is more fully described in my above-referenced copending patent applications Ser. Nos. 185,208 now U.S. Pat. No. 3,896,819, and 281,445, now U.S. Pat. No. 3,845,761, which are incorporated herein by reference. A diffusion dispenser of this type may be used to deliver a controlled flow of drug to the uterus for a prolonged period of time and is characterized by having drug present in an amount greater than its solubility limit in the liquid core and the core and wall materials selected such that the drug has a higher permeability in the core than in the wall. Such a dispenser can, if desired, give a constant (zero order time dependence) rate of drug release. A similar construction for dispenser 20 which may also be used but is not shown employs a solid carrier as described in my copending application U.S. Ser. No. 42,786 filed June 2, 1970, now U.S. Pat. No. 3,854,480, and entitled Drug Delivery System, which application is also incorporated herein by reference.

Device 10, as initially inserted in the uterus, with its "T" shape, clearly has a uterine-retentive configuration. Device 10 typically would be inserted by placing axial rod 19 in an inserter, causing cross bar 17 to bend down and nest around the inserter as device 10 is pushed through cervix 16. Difficulty may sometimes be experienced in the removal of device 10 from the uterus in its initial form with the possibility of damage to the endometrium. In accord with the present invention, however, device 10 undergoes a structural biotransformation in response to the environment of the uterus. Cross bar 17 and center rod 19 of device 10 are fabricated of a material, as will be set forth hereinafter, which is gradually soluble in uterine fluids and erodes slowly over a defined period of time. When bar 17 and rod 19 erode, they form innocuous products which are absorbed by or which pass from the uterus. Dispenser 20 does not erode, but is of a shape which is not retentive in the uterus so that when structural biotransformation takes place by bar 17 and rod 19 eroding, dispenser 20 is easily removed or is spontaneously discharged from the uterus.

The material for constructing bar 17 and rod 19 is selected to give a period of retention in the uterus prior to biotransformation which is correlated with the period of drug release. Optimally, the two time periods should be similar. If biotransformation to a non-retentive shape occurs substantially before the drug in dispenser 20 is exhausted, waste occurs. On the other hand, except in cases where it is desired to have an inert non-drug-releasing body present in the uterus, as is the case with some intrauterine devices, it is generally most suitable to discharge the remnants of device 10 from the uterus not substantially later than the end of the period of drug delivery so that a new device may be inserted to continue therapy.

Figure 3:
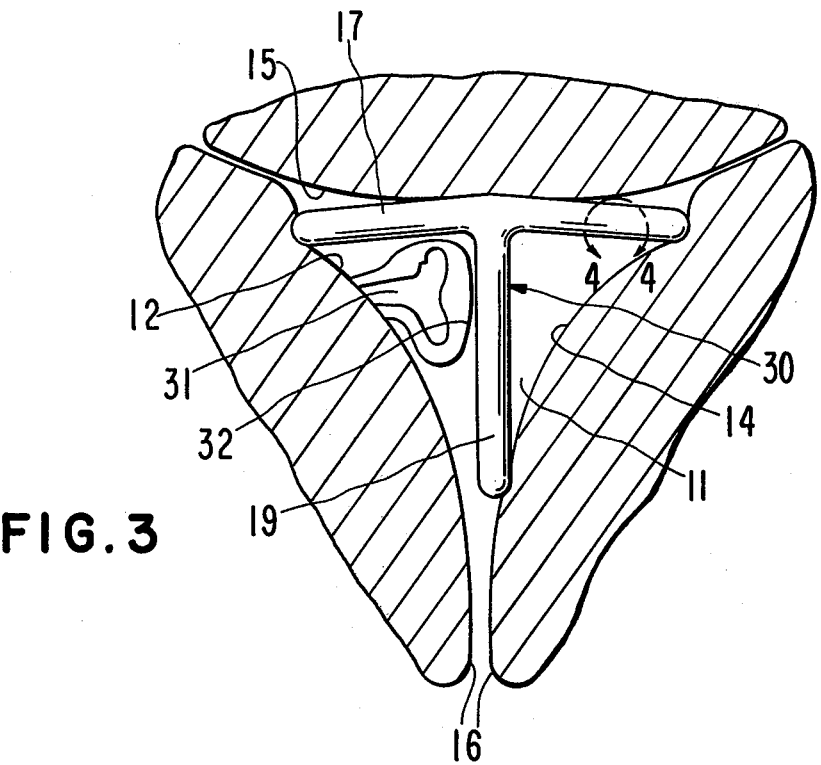
FIG. 3 is a cross-sectional elevational view of a uterus containing another embodiment of the device of this invention.
Figure 4:
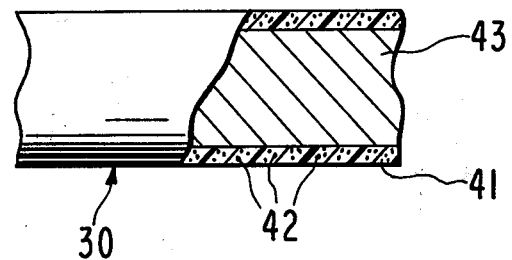
FIG. 4 is an enlarged cutaway section of the device depicted in FIG. 3.

Another variation of the improved intrauterine devices of the present invention may be found in FIG. 3 taken in conjunction with FIG. 4. In FIG. 3 an intrauterine device 30 of this invention is depicted in uterus 11 having walls 12 and 14 and fundus uteri 15. Walls 12 and 14 define cervix uteri 16 as well. Uterus 11 is illustrated also containing embryo 31 surrounded by amnion 32. Device 30 is shown in a typical uterine-retentive configuration, a T, and comprises a center bar 19 having joined thereto a perpendicularly intersecting cross bar 17. As illustrated in detail in FIG. 4, Device 30 comprises an outer covering 41 surrounding an inner core 43. Covering 41 gradually releases drug to the uterus by an erosion control mechanism, that is, particles or droplets of drug 42 are dispersed through a polymer which makes up the body of covering 41. This polymer is impermeable to the passage of drug and does not permit the drug to escape to any appreciable extent by diffusion, leaching, or like processes. The polymer is gradually soluble in the fluids of the uterine environment and gradually erodes, simultaneously uncovering and releasing entrapped drug 42. So long as the surface area of covering 41 remains essentially constant and the rate of erosion does too, the rate of drug release will remain essentially constant as well. A more complete description of controlled drug release through an erosion control mechanism may be found in copending U.S. Pat. application Ser. No. 318,831 of Richard Baker and Jorge Heller (Attorney docket number ARC 367) filed of even date and entitled Novel Delivery Device and now abandoned, and U.S. Ser. No. 248,168 of Alan S. Michaels filed Apr. 27, 1972, now U.S. Pat. No. 3,867,519, and entitled Bioerodible Drug Delivery Device, which applications are incorporated herein by reference. Device 30, initially, has a uterine-retentive configuration. It undergoes a biotransformation, for example, erosion or a loss of rigidity in the uterus, so as to transform device 30 from an initially retentive shape to either a non-retentive shape or to a plurality of fragments, which are non-retentive. This transformation occurs at about the time the delivery of drug 42 has been completed, in the case of device 30, at or about the time that uterine fluid-impermeable covering 41 is eroded and the fluids contact core 43. Core 43 may be a rapidly erodible material such as poly(vinyl alcohol), gelatin or the like or a material which rapidly loses its rigor when hydrated by contact with uterine fluids. Since covering 41 is liquid impermeable, no transformation of core 43 occurs until it has eroded. As soon as it has eroded, biotransformation rapidly follows. While device 30 of course is not so limited, in a preferred application it can release to the uterus a pregnancy interrupting drug or interceptive agent so as to bring about the expulsion or reabsorption of fertilized egg or embryo 31 by the uterus. This application of the device of the invention, as well as other applications, will be dealt with below.

Figure 5:
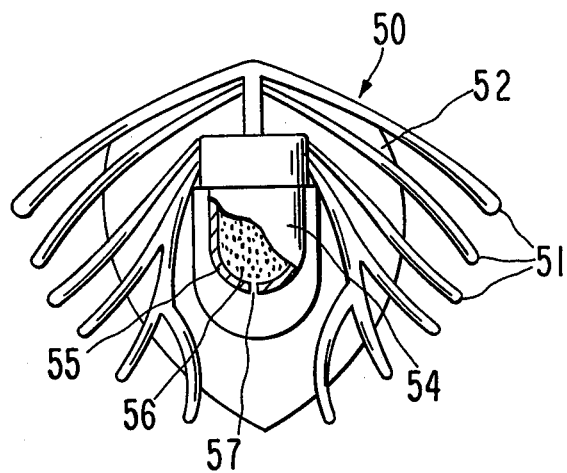
FIG. 5 is an enlarged partially cut away elevational view of an embodiment of the device of this invention.
Figure 6:
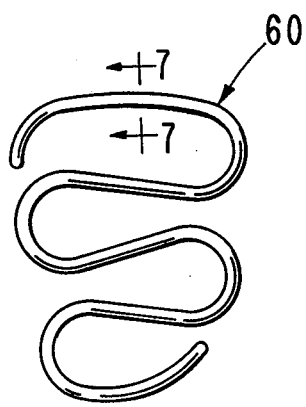
FIG. 6 is an elevational view of a further embodiment of this invention.
Figure 7:
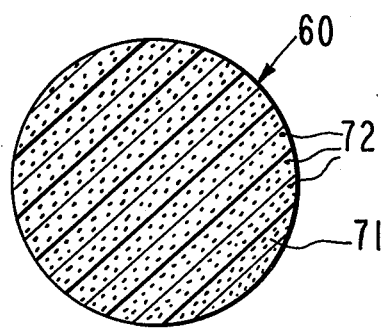
FIG. 7 is an enlarged cross-section of the device depicted in FIG. 6.

Turning to FIG. 5, another representative device in accord with this invention, device 50, is illustrated. Device 50 as shown is in a uterine-retentive shield or scarab-like form. Device 50 comprises a plurality of flexible ribs 51 joined together with a semi-rigid web 52 which gives the device its form. Attached in the center of device 50 is osmotic drug dispenser 54. Osmotic dispenser 54 is made up of a wall 55 of a material permeable to uterine fluids. Wall 55 forms a compartment in which drug 55 is contained. Drug 56 either alone or if required by means of admixture with a suitably osmotically effective compound causes uterine fluids to be drawn through wall 55. This flow of liquid causes drug 56 to be carried out of dispenser 54 via opening 57 and thus released to the uterus. Such drug dispensing devices are described in more detail in copending U.S. Patent application Ser. No. 259,469 of Theeuwes and Higuchi, entitled Dispensing Device, filed June 5, 1972, now U.S. Pat. No. 3,845,770, which application is herein incorporated by reference. When device 50 is placed in a uterus, drug 56 is released at a continuous rate over a defined prolonged period of time. The uterine environment functions to cause a biotransformation of device 50 so that, after a defined period in accord with this invention, the device takes a non-retentive form. In the case shown, this transformation takes the form of erosion of rigid web 52 so that only a flexible network of ribs 51 remain. This network is not strong enough to avoid collapsing and assuming a non-retentive form which may be easily and unobtrusively removed or expelled from the uterus. turning to FIG. 6, yet another representative variation of the invention is set forth - device 60. As detailed in the enlarged cross section of device 60 shown in FIG. 7, device 60 comprises a body of erodible impermeable polymer 71 having particles of drug 72 dispersed throughout.

When device 60 is initially inserted into a uterine environment, it has a retentive configuration. Polymer 71, which might well be the polymers described as suitable for coating 41 in FIGS. 3 and 4, gradually erodes in response to the uterine environment. As it does so, drug 72 is released. The products of erosion are absorbable molecular particles. Eventually the biotransformation is completed and the device has wholly dissolved and been absorbed.

Suitable Shapes

The present invention concerns generally the concept of an intrauterine device which undergoes biotransformation in use from a uterine-retentive shape to a non-retentive shape. The retentive and non-retentive shapes set forth in the figures are only representative and are not intended as limitations on the invention. Any retentive configuration may be used. Rather than to attempt to catalog the myriad retentive shapes known in the art, including bows, hearts, loops, comets, spirals, and the like, the text *Intrauterine Contraceptive Devices (A Compilation of Devices)* written by Shubeck et al and published in 1971 by Massachusetts Institute of Technology which, as the title implies, does so, is herein incorporated by reference as illustrating suitable retentive devices. Non-retentive shapes can range from simple rods, shaped products and small fragments, to molecularly-sized particles, all of which are not retained by the uterus.

Materials of Construction

A variety of materials are employed in the devices of the invention. They may be classified as follows. First, the devices all contain at least one material which reacts with the environment of the uterus to effect structural biotransformation. Second, the devices contain at least one material which plays a part in releasing drugs from the device at a controlled rate over a defined period of time. Depending upon the mode of drug release, this can be the same material employed to effect the structural biotransformation. Third, in many cases the devices contain non-erodible non-release rate controlling materials as structural members and the like. Finally, the devices all contain and release a suitable active agent (drug).

Turning first to biotransformable materials: Biotransformable materials suitable for fabricating the intrauterine devices are the materials that are non-toxic and non-irritating to the endometrium of the uterus, and which upon biotransformation produce end products that are also non-toxic, non-irritating and safely and easily eliminated from the body. As already noted, biotransformation can proceed by a number of mechanisms, for example:

a. by a physical change such as deflation or a loss of temper;

b. by a loss of structural integrity such as a loss of rigor or rigidity of a component; or c. by bioerosion of a structural member, said bioerosion being defined to include all mechanisms by which a unit structure disintegrates or breaks down from a unit structure or entity, to yield products of a molecular size which are thereafter absorbed by or passed from the uterus. Typical mechanisms include enzymatic action, oxidation or reduction, hydrolysis, ion exchange, dissolution by solubilization, and emulsion or micelle formation.

When biotransformation proceeds by deflation, suitable materials of construction include the distendable film-forming elastomers such as the natural and synthetic rubbers, butadiene-styrene block copolymers and the like which can form a deflatable structure. The deflation may proceed gradually as the inflating gas passes through the material or stepwise as a seal erodes to release the inflating gas.

When biotransformation proceeds through a loss of rigor or rigidity, a relatively rigid member becomes flexible and non-supportive. Such a biotransformation often proceeds through hydration of the relatively rigid member. Materials suitable for such a biotransformation include oriented poly(vinyl alcohol), dried gelatin, high hydrocarbon content poly(carboxylic acids) and hydrophilic lower alkyl acrylates and methacrylates such as hydroxyethylmethacrylate (Hydron S). These materials are representative of "flexibilizing" materials, that is materials which are initially rigid but which when exposed to the uterine environment gradually absorb uterine fluid, swell and lose their initial rigidity.

Biotransformation most commonly proceeds through bioerosion of a structural member formed of a bioerodible material. Exemplary materials to achieve such a mechanism include both natural and synthetic bioerodible materials such as (a) structural proteins and hydrocolloids of animal origin; (b) polysaccharides and other hydrocolloids of plant origin; and (c) synthetic polymers. Some of these matrix materials are suitable in their native form but others, particularly hydrocolloids, require insolubilization either by chemical modification, or physical modification, such as orientation, radiation cross-linking, etc. Exemplary of the structural proteins are: native and modified collagens, muscle proteins, elastin, keratin, resilin, fibrin, etc. Exemplary of polysaccharides and plant hydrocolloids are: algin, pectin, carrageenin, chitin, chondroitin sulfate, Agar-agar, Guar, locust bean gum, gum arabic, gum Karaya, tragacanth, gum Ghatti, starch, oxystarch, starch phosphate, carboxymethyl starch, sulfaethyl starch, aminoethyl starch, amido ethyl starch, starch esters such as starch maleate, succinate, benzoate and acetate, and mixtures of starch and gelatin; cellulose and its derivatives such as modified cellulosics, such as partially hydroxyethylated cotton obtained by the treatment of cotton with ethylene oxide or partially carboxymethylated cotton obtained by the treatment of cotton with caustic and choroacetic acid. Exemplary of synthetic polymers are: poly(vinyl alcohol), poly(ethylene oxide), poly(acrylamide), poly (vinyl pyrrolidone), poly(ethyleneimine), poly(vinyl imidazole), poly(phosphate), synthetic poly(peptides), poly(vinyl alkyl ether), poly(acryl-and poly-methacrylamides), and copolymers of acrylamide and methacrylamide with up to 40% by weight of N-methylene bisacrylamide or N,N-dimethylol urea; poly(alkyl aldehydes), water soluble hydrophilic polymers of uncross-linked hydroxyalkyl acrylates and methacrylates, poly(alkylene carbonates), and the like. The list is illustrative.

Without intent to limit the scope of the present invention, the following materials are most useful as biotransformable materials in the intrauterine drug delivery devices, when the biotransformation proceeds through the preferred erosion mechanism of this invention.

1. Cross-Linked Gelatin

Gelatin is obtained by the selective hydrolysis of collagen by means well known to those skilled in the art and comprises a complex mixture of water soluble proteins of high molecular weight. As used herein, the term cross-linked gelatin means the reaction product of gelatin or a gelatin derivative with a cross-linking agent reactive with either the hydroxyl, carboxyl or amino functional groups of the gelatin molecule and substantially unreactive with the peptide linkage of the gelatin molecule, the product of reaction having an average molecular weight of from 2,000 to 50,000 between cross-links, although higher values can be employed. Such a product is degradable in the environment of the uterus over a prolonged period of time.

Cross-linked gelatin materials are well known to those skilled in the art and can be prepared by reacting the cross-linking agent with gelatin under suitable reaction conditions. The degree to which the gelatin is cross-linked is dependent upon the processing conditions employed to carry out the reaction and markedly affects its characteristics with regard to the time required in order for the material to biodegrade in the eye. The rate and, therefore, the degree of cross-linking of the gelatin is primarily determined by: (1) the effective concentration of reactive groups present; (2) reaction time; (3) temperature at which the reaction is carried out; and (4) pH of the reaction environment. The choice of the particular conditions will of course depend on the properties desired for the end product as hereinafter discussed.

Exemplary of suitable cross-linking agents are: aldehydes, such as monoaldehydes, e.g., $C_1$-$C_4$ alkanones, e.g., acetaldehyde, formaldehyde, acrolein, crotonaldehyde, 2-hydroxy adipaldehyde; dialdehydes, such as starch dialdehyde paraldehyde, furfural and aldehyde bisulfite addition compounds such as formaldehyde bisulfite; aldehyde sugars, e.g., glucose, lactose, maltose, and the like; ketones such as acetone, methylolated compounds such as dimethylol urea, trimethylol melamine; "blocked" methylolated compounds such as tetra(methoxymethyl) urea, melamine; and other reagents such as $C_1$-$C_4$ disubstituted carbodiimides; epoxides such as epichlorohydrin, Eponite 100 (Shell); para-benzene quinone; dicarboxylic acids, e.g., oxalic acid, disulfonic acids, e.g., m-benzene disulfonic acid; ions of polyvalent metals, e.g., chromium, iron, aluminum, zinc, copper; amines such as hexamethylene tetramine; and aqueous peroxydisulfate. See H. L. Needles, J. Polymer Science, Part A-1, 5 (1) 1 (1967).

Still another suitable method for cross-linking gelatin is that using irradiation; see for example Y. Tomoda and M. Tsuda, J. Poly. Sci., 54, 321 (1961).

The reactive groups present in gelatin, i.e., hydroxyl, carboxyl and amino functions are present per 100 grams of high quality gelatin in the following approximate amounts: 100, 75 and 50 meq of each of these groups, respectively. The number of reactive sites do not vary appreciably from one gelatin to another, i.e., Type A or B gelatins, unless major hydrolytic breakdown has occurred. These quantities may serve as a general guide in determining the amount of cross-linking agent to be used. For example, using formaldehyde as the cross-linking agent, concentrations thereof from 0.01% to 50% by weight, based on the weight of the gelatin in combination with reaction times of 0.1 hours to 5 days and at temperatures of from 4.0°C to 35°C will yield suitable products, the exact combination of concentration, temperature and time depending on the desired dissolution rate. General information on cross-linked gelatin can be found in *Advances in Protein Chemistry*, Vol. VI, Academic Press, 1951, "Cross Linkages in Protein Chemistry", John Bjorksten.

2. Polyesters

Polyesters of the general formula:

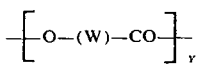   I and mixtures thereof, wherein:
W is a radical of the formula —CH$_2$—; or

and;
Y has a value such that the molecular weight of the polymer is from about 4,000 to 100,000 may also be used.

These polymers are polymerization condensation products of monobasic hydroxy acids of the formula:

$C_nH_{2n}(OH)COOH$   II wherein *n* has a value of 1 or 2, especially lactic acid and glycolic acid. Also included are copolymers derived from mixtures of these acids. The preparation of polymers of formula I per se, forms no part of the present invention. Several procedures are available and reported by Filachione et al, *Industrial and Engineering Chemistry*, Vol. 36, No. 3, pp. 223–228, (March 1944) Tsuruta, et al, *Macromol. Chem.*, Vol. 75, pp. 211–214 (1964), and in U.S. Pat. No. 2,703,316; 2,668,162; 3,297,033; and 2,676,945.

3. Cross-Linked Anionic Polyelectrolytes

Cross-linked substantially water-insolubilized polymeric coordination complexes may be used as biotransformable materials. These materials consist of anionic polyelectrolyte polymers such as polysaccharides, natural gums, for example, algin and synthetic polyelectrolytes, for example, poly (vinyl methylol sulfonic acid) cross-linked with non-toxic polyvalent metal ions such as zinc II or nickel II ions.

These materials, and the methods for their preparation and fabrication, are the sole invention of Alan S. Michaels. They are more fully described and claimed in his copending application Ser. No. 248,168 filed on Apr. 27, 1972, and now U.S. Pat. No. 3,867,519, entitled Bioerodible Drub Delivery Device, which application is herein expressly incorporated by reference.

4. Polyacids

Polyacids characterized as being hydrophobic when unionized and as having a specified proportion of carboxylic hydrogens may also be employed as erodible biotransformable materials.

Suitable poly(carboxylic acids) are the hydrophobic polyacids which are represented by the general formula:

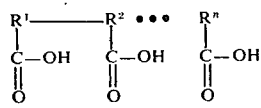   III wherein: the R's are organic radicals independently selected to provide, on average, from 8 to 22 total carbon atoms for each carboxylic hydrogen. Variations of this ratio within this range can vary the erosion rates of these polymeric acids. Organic radicals represented by $R^1$, $R^2$, ... $R^n$ may be selected from hydrocarbon radicals and hetero-atom containing radicals.

A preferred group of materials from which the biotransformable materials may be selected comprise hydrophobic polymers of an acid selected from acrylic acid, lower alkyl acrylic acids of from 4 to 6 carbon atoms per monomeric unit, and maleic acid either along or copolymerized with up to about 2 moles per mole of acid of a copolymerizable olefinically unsaturated group such as ethylene or lower (1 to 4 carbon) alkyl vinyl ethers wherein from about 20% to 90% of the acid groups have been esterified with an alkanol of from 1 to about 10 carbon atoms and wherein the ratio of total carbon atoms to acidic carboxylic hydrogens is in the range of from about 9:1 to about 20:1.

More specifically, good results are obtained with poly(carboxylic acids) which comprise the hydrophobic partially esterified copolymers of acrylic acid, methacrylic acid or maleic acid with from 0.2 to 1.5 moles, per mole of acid of ethylene or lower (1–4 carbon) alkyl vinyl ether having from about 35% to about 70% of their total carboxylic groups esterified with lower alkanol of from about 3 to about 10 carbon atoms, said copolymers having a carbon to acidic carboxylic hydrogen ratio of from about 10:1 to about 15:1. These polyacids, their preparation and application to drug delivery devices are disclosed in substantial detail in commonly assigned copending application Ser. No. 318,831 and now abaondoned, of Jorge Heller and Richard Baker, entitled Novel Delivery Device, filed of even date with this present application and having Docket No. ARC 367. This application is expressly incorporated herein by reference. The foregoing materials are intended to be illustrative, others may be employed as biotransformable materials if desired.

Turning now to the materials which effect a controlled release of drugs from the devices of the invention, first the mechanisms of drug release should be considered. Any mechanism which will bring about a controlled release of drug and which may be adapted to a uterine-insertive size may be used. Three drug release mechanisms, described with reference to the Drawings, are eminently suited for employment in the present invention. These drug release mechanisms are:

1. Diffusion control release - wherein drug is released by passing at a controlled rate through a membrane having a limited permeability to the drug;

2. Erosion control release - wherein drug is released by gradual erosion of an entrapping encompassing matrix; and 3. Osmotic pumping release - wherein drug is released by being gradually forced under osmotic pressure from a container.

When diffusion control release is employed, the device of the invention will include a release-rate-controlling membrane through which the drug will pass by diffusion and optionally a liquid or solid core through which the drug is permeable at a higher rate than the rate of release through the rate-controlling membrane.

The materials suitable for fabricating the rate controlling membranes are generally those materials capable of forming walls, with or without pores, through which the drug can pass at a controlled rate by the process of diffusion.

Exemplary naturally occurring or synthetic materials suitable for fabricating a permeation control wall are drug rate release controlling materials such as poly(methylmethracrylate), poly(butylmethacrylate), plasticized or unplasticized poly(vinylchloride), plasticized nylon, plasticized soft nylon, plasticized poly(ethylene terephthalate), natural rubber, poly(isoprene), poly(isobutylene), poly(butadiene), poly(ethylene), poly(tetrafluoroethylene), poly(vinylidene chloride), poly(acrylonitrile), cross-linked poly (vinylpyrrolidone), poly(trifluorochlorethylene), poly (4,4'-isopropylidene diphenylene carbonate), and the like. Also, by way of non-limiting example, copolymers such as ethylenevinylacetate, vinylidene chloride acrylonitrile, vinyl chloride diethyl fumarate and the like. Examples of other materials include silicone rubbers, especially the medical grade poly(dimethylsiloxanes), and silicone-carbonate copolymers; hydrophilic polymers such as the hydrophilic hydrogels of esters of acrylic and methacrylic acid as described in U.S. Pat. Nos. 2,976,576 and 3,220,960 and Belgian Patent No. 701,813, modified insoluble collagen, cross-linked poly(vinylalcohol), cross-linked partially hydrolyzed poly(vinylacetate), and surface treated silicone rubbers as described in U.S. Pat. 3,350,216. Other polymeric membranes that are biologically compatible and do not adversely affect the drugs can be used.

Materials suitable for use as the optional carriers in diffusion control systems include liquid or solid materials of natural or synthetic origin having a permeability to drug which is higher than the permeability of the rate controlling membranes.

Representative drug permeable liquid carriers include ethylene glycol, diethylene glycol, ethylene glycol monomethyl ether, mixed binary liquid systems such as ethyl alcohol:water, fats and oils of plant, animal and marine origin, liquid fatty acids such as caproic acid, silicone oil, medical oil, and sterile water or saline.

Suitable drug-permeable solid carriers include solids having a higher drug permeability than the release rate controlling membranes, for example, the dimethylsilicones, silicone carbonate polymers, hydrophilic hydrogels of esters of acrylic and methacrylic acid, and the like.

When an erosion control release mechanism is employed, particles, including grains or droplets, of drug are dispersed through a body of drug-impermeable erodible polymer. Suitable polymers for this purpose include essentially hydrophobic impermeable film-forming polymers. Two classes of polymers which are quite effective are the polyesters and hydrophobic polyacids described above as suitable for use as biotransformable materials. The polyacids are preferred materials for effecting erosion control of drug release.

When osmotic delivery is the mode of drug release, a wall of material selectively permeable to uterine fluids is employed. Typical materials for forming an osmotic wall include cellulose acetate, agar acetate, and cellulose acetate derivatives, hydroxylated ethylene-vinyl acetate and derivatives of poly(styrene). With osmotic delivery, it is often required to employ an osmotically effective solute to draw uterine fluid through the wall into the device. Typical solutes are sodium chloride, magnesium chloride and sulfate, potassium sulfate and the like. A fuller description of materials for and the operation of an osmotic delivery device are given in incorporated application Ser. No. 259,469, now U.S. Pat. No. 3,845,770 of Theeuwes and Higuchi.

The third major group of materials for use in the devices of this invention comprise inert structural materials. These components are optionally employed. These materials include any biocompatible material and may range from gold and stainless steel to poly-(ethylene), poly(urathane), fiber glass, nylon, poly(isoprene) and cardboard.

The final materials of construction are drugs, which are incorporated in and released from the biotransformable intrauterine devices. The term "drug" broadly includes physiologically or pharmacologically active substances for producing effects in mammals, including humans and primates; avians, sport or farm animals such as horses, dogs, cats, cattle, sheep and the like; or laboratory animals such as mice, monkeys, rats, guinea pigs and the like.

While the devices of this invention operate with special effectiveness with drugs which have a localized effect in or upon the uterus, systemically active drugs which act at a point remote from the uterus may be administered as well and are included within the term drugs. Thus, drugs that can be administered by the intrauterine device of the invention include, without limitation: drugs acting on the central nervous system such as, hypnotics and sedatives such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and $\alpha$-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxazid, nialamide, phenelizine, imipramine, tranylcypromine, pargylene and the like; tranquilizers such as chloropromazine, promazine, fluphenazine reserpine, deserpidine, meprobamate, benzodiazepines such as chlordiazepoxide and the like; anti-convulsants such as primidone, diphenylhydantoin, ethotoin, pheneturide, ethosuximide and the like; muscle relaxants and anti-parkinson agents such as mephenesin, methocarbomal, trihexylphenidyl, biperiden, levo-dopa, also known as L-dopa and L-$\beta$-3-4-dihydroxyphenylalanine, and the like; analgesics such as morphine, codeine, meperidine, nalorphine and the like; anti-pyretics and anti-inflammatory agents such as aspirin, salicylamide, sodium salicylamide and the like; local anesthetics such as procaine, lidocaine, naepaine, piperocaine, tetracaine, dibucaine and the like; anti-spasmodics and the anti-ulcer agents such as atropine, scopolamine, methscopolamine oxyphenonium, papaverine; anti-microbials such as penicillin, tetracycline, oxytetracycline, chlorotetracycline, chloramphenicol, sulfonamides and the like; anti-malarials such as 4-aminoquinolines, 8-aminoquinolines and pyrimethamine; hormonal agents such as prednisolone, cortisone, cortisol and triamcinolone; sympathomimetic drugs such as epinephrine, amphetamine, ephedrine, norephineprine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; anti-parasitic agents such as bephenium hydroxynaphthoate and dichlorophen, dapsone and the like; neoplastic agents such as mechlorethamine, uracil mustard, 5-fluorouracil, 6-thioguanine, procarbazine and the like; hypoglycemic drugs such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents.

The devices of this invention deliver with special effeciency drugs for locally treating uterine or vaginal disorders, such as endometritus, vaginitis and irregular vaginal bleeding. Such drugs include, for example, antibiotics, hormones and the like. The devices also function with special efficiency delivering progestational substances that have anti-fertility properties and estrogenic substances that have anti-fertility properties. These substances can be of natural or synthetic origin. They generally possess a cyclopentanophenanthrene nucleus. The term progestational substance as used herein embraces "progestogen" which term is used in the pharmaceutically acceptable steroid art to generically describe steroids possessing progestational activity, and the former also includes "progestins", a term widely used for synthetic steroids that have progestational effects. The active anti-fertility progestational agents that can be used to produce the desired effects in mammals, including humans, and primates include without limitations: pregn-4-ene-3,20-dione, also known as progesterone; 19-nor-pregn-4-ene-3,20-dione; 17-hydroxy-19-nor-17$\alpha$-pregn-5(10)-3n3-20-yn-3-one; dl-11$\beta$-ethyl-17-ethinyl-17-ethinyl-17-$\beta$-hydroxygon-4-ene-3-one; 17$\alpha$-ethinyl-17-hydroxy-5(10)-estren-3-one; 17$\alpha$-ethinyl-19-norestosterone; 6-chloro-17-hydroxypregna-4,6-diene-3,20-dione; 17$\beta$-hydroxy-6$\alpha$-methyl-17-(1-propynyl)androst-4-ene-3-one; 9$\beta$,10$\alpha$-pregna-4,6-diene-3,20-dione; 17-hydroxy-17$\alpha$-pregn-4-en-20-yne-3-one; 19-nor-17$\alpha$-pregn-4-3n-20-yen-3$\beta$,17-dial; 17-hydroxy-pregn-4-ene-3,20-dione; 17$\alpha$-hydroxy-progesterone; 17-hydroxy-6$\alpha$-methylpregn-4-ene-3,20-dione; mixtures thereof, and the like.

The estrogenic anti-fertility agents useful herein also include the compounds known as estrogens and the metabolic products thereof that possess anti-fertility properties or that are converted to active anti-fertility agents in the uterine environment. Exemplary estrogenic compounds include $\beta$-estradiol, $\beta$-estradiol 3-benzoate, 17-$\beta$-cyclopentanepropionate estradiol, 1,3,4(10)-estratriene-3,17$\beta$-diol dipropionate, estra-1,3,5(10)-triene-3,17-$\beta$-diol valerate, estrone, ethinyl estradiol, 17-ethinyl estradiol-3 methyl ether, 17-ethinyl estradiol-3-cyclopentoether, estriol, mixtures thereof, and the like.

In a most preferred application, devices of this invention contain and deliver interceptive agents for pregnancy termination. Included within the group entitled interceptive agents are all drugs which cause the premature expulsion or absorption of a fetus by the uterus. Interceptive agents include materials like sodium chloride and fatty acids which induce expulsion of a fetus by causing uterine tonicity and pH imbalance respectively. Other interceptive agents include drugs for inducing uterine contractions such as the oxytocic agents, for example, oxytocin, ergot alkaloids such as ergonovine and methylergonomine, quinine, quinidine, histamine, sparteine, and the prostaglandins. The E and F series prostaglandins, especially prostaglandins $E_1$, $E_2$ and $F_{2\alpha}$, are very suitably delivered by devices of this invention to interrupt pregnancy. A full description of useful prostaglandins and their application in intrauterine devices is given in the copending U.S. patent application Ser. No. 318,890, now U.S. Pat. No. 3,888,945, filed of even date with this application by Peter Ramwell (Attorney docket no. IR 44), entitled Intrauterine Drug Delivery Device, which application is herein incorporated by reference.

The amount of drug present in the device is dependent upon dosage requirements and the length of time the device is to be in place in the uterus and may vary from a single dose of a very potent drug, which may be as little as a few micrograms, to an amount sufficient for several hundred or even a thousand doses of a less potent drug, such as up to several grams (for example, 5 grams). The devices of this invention are intended to release drugs locally to the uterus over defined prolonged periods of time, that is, for periods of from about 3 hours to 30 days or longer. With the progestational and estrogenic substances, delivery times of from about 1 day to 30 days or a year or more are preferred, with dosage rates of from about 10 to 200 mg per day being preferred, thus making it desirable to incorporate at least from about 10 mg to about 6 grams of these substances in a delivery device. When interceptive agents are administered for pregnancy terminating purposes, it is preferred to administer the agents over a period of from about 4 hours to about 24 hours. When prostaglandins are the interceptive agents, they are delivered at a rate of about 1 microgram/minute to about 25 micrograms/minute. Thus, considering the dosage rate and period, the loading of prostaglandins as interceptive agents in the present devices may suitably vary from about 250 micrograms up to as much as about 100 milligrams. Preferably the loading of prostaglandin would be between about 1 milligram and about 100 milligrams. Similar drug loadings could be determined for the many other drugs suitably delivered by these devices based on the dosage period and rate desired.

The intrauterine devices gradually undergo biotransformation in the uterus and release their drug. The rate of biotransformation will depend in part on the recipient's temperature (generally from about 35° to 43°C), uterine pH (generally pH 7-8) and the amount of uterine fluids presently available to contact the device.

The rate of biotransformation and drug release of materials employed in the invention can be determined experimentally in vitro by testing them under simulated environmental conditions. For example, the rate of biotransformation of a material in uterine fluids may be measured by placing a small weighed sample of the material in physiological saline solution - a solution of pH about 7.4 (simulated uterine fluids) at body temperature (37°C), agitating for a timed interval, and periodically measuring the amount of material eroded into the solution. Similarly, a rate of biotransformation through softening of a material may be derived in vitro by placing the material in simulated uterine fluid and measuring its flexibility. To accurately predict in vivo results, it is necessary to multiply the in vitro rates by an experimentally determined constant which takes into account differences in stirring rate and fluid volumes between the living body and the in vitro test apparatus. This constant may be derived in the cases just set forth by placing a plurality of small weighted samples of material in a plurality of uteri and sequentially, over a period of time, removing and weighing or flex-testing the samples. The rates thus determined, divided by the rates observed in vitro with the same material, equal the necessary constant.

For a more complete understanding of the nature of this invention, reference should be made to the following examples which are given merely as further illustrations of the invention, and are not to be construed in a limiting sense.

EXAMPLE I

A biotransformable intrauterine device which achieves biotransformation through erosion is prepared.

1. An erodible hydrophobic polycarboxylic acid is prepared as follows.

12.6 grams (0.10 equivalents) of ethylene-maleic anhydride copolymer (Monsanto EMA, Grade 31) is stirred with 0.04 moles of n-pentyl alcohol at 100°–110°C for 7 hours. The solution is cooled to room temperature and methylene chloride is gradually added to the cloud point. Then more methylene chloride is added to precipitate the product (total vol. 3l). The precipitate is thoroughly leached with the methylene chloride. The solvent is decanted and the product dissolved in 75 ml warm acetone. Methylene chloride is added to the cloud point. Then more methylene chloride is added to precipitate the product (total vol. 2L). The precipitate is then thoroughly leached with the methylene chloride. The solvent is decanted and the product dissolved in 75 ml acetone. The solution is transferred to a poly(propylene) container and the solvent is removed under vacuum at 50°C to yield the polymer product. The infrared spectrum of the polymer shows broad bands at 1680 and 1780cm$^{-1}$, indicative of ester carboxyl. Titration with base shows that the pentyl half ester of the maleic acid copolymer has been formed, and thus the ratio of total carbons to ionizable hydrogens on average is 11:1.

2. A β-estradiol-containing material is prepared as follows.

5.4 grams of the half ester polymer of part A is dissolved in 15 ml of acetone, with stirring at 25°C. 0.6 grams of crystalline β-estradiol are dispersed in the solution with stirring. The resulting viscous dispersion is cast in a polyethylene mold into a rod of wet diameter of about 2.0 mm. The cast rod is allowed to dry thoroughly to yield a 1 mm diameter dry rod. The resulting rod is removed from the die. It weighs about 30 mg per cm and contains about 3 mg of β-estradiol per cm.

3. An intrauterine device is prepared and used as follows.

A 2 cm long portion of the rod of part B is affixed with epoxy glue to a 2 cm long piece of non-erodible poly(ethylene) to form a I shaped device. The cross bar is erodible, the center bar is non-erodible. The center bar of this device is inserted in a straight flexible plastic inserter. The cross bar arms are flexible and bend down so that the device is easily inserted into a human uterus. The T shape is a uterine-retentive configuration.

The bar of poly(carboxylic acid) is hydrophobic and impermeable to the absorption of uterine fluids or to the passage of drug. The bar of poly(carboxylic acid) gradually erodes and as it does so releases an average of about 30 micrograms of β-estradiol per hour for about 200 hours. After about 180–200 hours, the erosion of the cross bar has progressed to a point that the cross bar breaks loose from the center bar. The center bar alone is not a uterine retentive form and is expelled from the uterus during or before the user's next menstrual period.

EXAMPLES II AND III

The prepartion set forth in Example I, parts A and B, is repeated 2 times with one variation. The molar excess of n-pentanol employed in Example 1 is replaced with a similar amount of other alkanols as follows:

| Example | Alkanol |
|---|---|
| 2 | n-butanol |
| 3 | n-hexanol |

The ratio of total carbon atoms to ionizable carboxylic hydrogens in each of the resulting half esters is as follows:

| Example | Ratio: Carbons Ionizable Hydrogens |
|---|---|
| 2 | 10 |
| 3 | 12 |

The material of Example II erodes about twice as fast as the material of Example I, while the material of Example III erodes about one-half as fast as the material of Example I. A 4 cm piece of the material of Example II is shaped into a '7' configuration while an 8 cm piece of the material of Example III is bent into an "S" shaped loop. Both shapes prove retentive when inserted into a human uterus. The first erodes to a series of small fragments over a period of about 100 hours, releasing drug at an average rate of about 120 micrograms/hour. The latter requires about 400 hours to erode. At the end of the erosion, the devices have biotransformed to a non-retentive configuration.

EXAMPLE IV

A biotransformable drug delivering intrauterine device having a drug release rate controlling wall permeable to the passage of drug and surrounding a reservoir comprised of a drug and a liquid core for releasing progesterone is manufactured as follows: a liquid dispersion drug carrier is prepared by intimately contacting and blending in a rotating mill 25% by weight of progesterone and 10% by weight of barium sulfate with a mixture comprising 3 parts by weight of Dow-Corning 382 elastomer resin, low molecular weight prepolymer liquid silicone and 1 part by weight of Dow-Corning 360 medical fluid silicone oil. The liquid dispersion is permeable to the drum and the drug is sparingly soluble therein. Next, the liquid dispersion is injected into a 2 cm length of ethylene vinyl acetate copolymer tubing comprised of 9% by weight of vinyl acetate and having an inside diameter of 0.075 inches and an outside diameter of 0.110 inches. The ends of the tubing are heat sealed.

This 2 cm long tube is not a uterus-retentive configuration. The tube is fabricated into a retentive T shape in the following manner.

First, an erodible polyvalent metal ion cross-linked polyelectrolyte is prepared. Seventy grams of sodium alginate (Keltone, Kelco Co., KT-9529-21) is dissolved in 3000 ml of distilled water to yield a slightly viscous solution. In a separate preparation, 100 grams of zinc chloride is dissolved in 4000 ml of distilled water and the pH is adjusted to 3 with concentrated hydrochloric acid. The zinc chloride solution is transferred into a high speed blender. To this solution is added the sodium alginate solution. The mixture is stirred and allowed to stand overnight. The precipitate is then washed continuously with distilled water to a negative silver chloride test. The aqueous suspension of the sodium chloride-free zinc alginate is isolated by lyophilization and vacuum-dried at 40°C overnight. Into a blender containing 1000 ml of 1.2% ammonium hydroxide solution is added 50 grams of zinc alginate previously prepared. Agitation is continued until the complete dissolution of the zinc alginate results. The resulting viscous dispersion is drawn on a glass plate with a wet thickness of ca. 200 mils. The cast plate is allowed to dry thoroughly. The resulting film is about 60 mils thick. It is removed from the plate and is cut into 0.5 cm wide strips. A 2 cm long strip of the alginate material is attached to the heat sealed tube previously prepared with adhesive to yield a uterine-retentive T configuration. When the device is placed in a uterus, progesterone is released through the ethylene vinyl acetate tube by diffusion at a rate of about 20–30 micrograms per day. This release continues at this rate for a prolonged period of time. The metal ion cross-linked polyelectrolyte cross bar is gradually eroding in the uterus by a process of metal ion exchange. Monovalent metal ions from uterine fluids gradually displace the cross linking polyvalent ions resulting in solubilization of the polyelectrolyte. After about 30–40 days enough of the polyelectrolyte has solubilized to render the cross bar so flexible that it no longer functions to retain the device in the uterus. The device is then non-retentive and is expelled by the uterus.

EXAMPLES V – VII

Three biotransformable intrauterine devices adapted to release interceptive agents to terminate pregnancy are prepared as follows:

To three 10 gram portions of the n-butanol half ester material of Example II are added respectively: 1.0 gram of the prostaglandin known as $PGF_{2\alpha}$ and 0.2 and 0.4 grams of $PGE_2$.

Each of these mixtures is dissolved in acetone. A milti-armed, T shaped intrauterine device, made with a flexible center bar and cross arms of the erodible pentyl half ester of Example I has the lower end of its center bar repeatedly dipped into the first of these solutions and dried. 100 mg of ester and prostaglandin is deposited. Second and third multi-armed T devices are dipped into the second and third solution. 100 mg of each of these polymer and prostaglandin mixtures are deposited. It would be possible, of course, to deposit more, say 500 mg, or less, say 60 mg, of the mixtures.

The three devices are gently inserted into uteri of three first trimester pregnant women. The devices release respectively:

10 micrograms/minute of $PGF_{2\alpha}$
2 micrograms/minute of $PGE_2$, and
4 micrograms/minute of $PGE_2$ all for periods of about 24 hours. After another 24 – 48 hours, the erodible cross arms begin to drop off and the devices are expelled.

These releases of prostaglandins are sufficient to cause uterine contractions and are suitable for effecting therapeutic pregnancy termination. Varying the concentration of prostaglandin from about 1% to about 20% basis polymer would give delivery rates of from about 1 microgram/minute to about 20 microgram/minute.

EXAMPLE IX

An aqueous solution 20% of polyvinyl alcohol is prepared. This solution is formed into an oriented 30 gauge fiber suitable spinnerette and dried and drawn. A large number of these fibers are bundled together and placed in a heated die. There they are pressed at 800 psi and 250°C for 4 minutes to yield a 0.15 inch diameter rod of oriented polyvinyl alcohol. This rod, while deformable and shapable, is relatively rigid. A 7½ inch length of this material is bent into a mold loop-shaped in accordance with FIG. 7. Heat is applied and the rod assumes the mold's uterine retentive shape.

To the small end of this loop device is attached an osmotic drug dispenser. This dispenser consists of a 1 cc container constructed of the semi-permeable material, cellulose acetate. Located within the container is a solution of oxytocin and 0.5 gram of magnesium chloride. There is a single opening in the container, a 0.01 cm diameter hole. When such a dispenser is placed in an aqueous environment, it absorbs water and forces oxytocin-containing solution out of the 0.01 cm hole. The rate of pumping is substantially constant. The rate of oxytocin delivery tends to decrease with time as the inflowing water causes dilution. When such a dispenser is placed in a human uterus, an amount of oxytocin sufficient to induce uterine contractions is delivered for about 18–24 hours. The dispenser is retained in the uterus by the uterine-retentive loop of polyvinyl alcohol to which it is affixed. At about the end of this defined period of drug administration, or within about 6 hours after the end of the drug administration, the oriented polyvinyl alcohol loop has absorbed enough water to loose its rigidity and, hence, its uterine retentive characteristics. The device may then be easily removed or may be spontaneously expelled from the uterus.

What is claimed is:

1. A drug dispensing intrauterine device, shaped and adapted for insertion and positioning in the uterine cavity, with the device comprising in combination:
    a. a drug
    b. a delivery means adapted for insertion into the uterine cavity and for dispensing a therapeutically effective amount of drug to the uterine cavity over a defined period of time, and
    c. retention means for retaining the delivery means within the uterine cavity throughout the defined period of drug dispensing time, said retention means having an initial unit structural configuration sahped and adapted for insertion and positioning in the uterine cavity including means formed of a member selected from the group consisting of protein, collagen, elastin, keratin, resilin and fibrin that undergo biotransformation in the uterine cavity to a different and nonuterine-retentive configuration whereby at the completion of said defined period of drug dispensing time, said drug dispensing device is facilely removed or spontaneously eliminated from the uterine cavity.

2. The device according to claim 1 wherein the drug is a member selected from the group consisting of progestational and estrogenic steroids.

3. A drug dispensing intrauterine device, shaped and adapted for insertion and positioning into the uterine cavity, with the device comprising in combination:
 a. a drug
 b. a delivery means adapted for insertion into the uterine cavity and for dispensing a therapeutically effective amount of drug to the uterine cavity over a defined period of time, and
 c. retention means for retaining the delivery means within the uterine cavity throughout the defined period of drug dispensing time, said retention means having an initial unit structural configuration shaped and adapted for insertion and positioning in the uterine cavity including means formed of a member selected from the group consisting of a noncross-linked polysaccharide, algin, pectin, carrageenin, chitin, chondrotin sulfate, agar-agar, guar, locust bean gum, gum arabic, gum karaya, tragacanth and gum ghatti that undergo biotransformation in the uterine cavity to a different and nonuterine-retentive configuration and shape whereby at the completion of said defined period of drug dispensing time, said drug dispensing device is facilely removed or spontaneously eliminated from the uterine cavity.

4. The device according to claim 3 wherein the drug is a member selected from the group consisting of progestational and estrogenic steroids.

5. A drug dispensing intrauterine device, shaped and adapted for insertion and positioning into the uterine cavity, with the device comprising in combination:
 a. a drug
 b. a delivery means adapted for insertion into the uterine cavity and for dispensing a therapeutically effective amount of drug to the uterine cavity over a defined period of time, and
 c. retention means for retaining the delivery means within the uterine cavity throughout the defined period of drug dispensing time, said retention means having an initial unit structural configuration shaped and adapted for insertion and positioning in the uterine cavity including means formed of a member selected from the group consisting of starch, oxystarch, starch phosphate, carboxymethyl starch, sulfaethyl starch, aminoethyl starch, amidoethyl starch, starch esters, starch maleate, starch succinate, starch benzoate, starch acetate and mixtures of starch and gelatin that undergo biotransformation in the uterine cavity to a different and nonuterine-retentive configuration and shape whereby at the completion of said defined period of drug dispension time, said drug dispensing device is facilely removed or spontaneously eliminated from the uterine cavity.

6. The intrauterine dispensing device according to claim 5 wherein the drug is a member selected from the group consisting of progestational and estrogenic steroids.

7. A drug dispensing intrauterine device, shaped and adapted for insertion and positioning into the uterine cavity, with the device comprising in combination:
 a. a drug
 b. a delivery means adapted for insertion into the uterine cavity and for dispensing a therapeutically effective amount of drug to the uterine cavity over a defined period of time, and
 c. retention means for retaining the delivery means within the uterine cavity throughout the defined period of drug dispensing time, said retention means having an initial unit structural configuration shaped and adapted for insertion and positioning in the uterine cavity including means formed of a member selected from the group consisting of cellulose, hydroxyethylated cotton, carboxymethylated cotton and mixtures thereof that undergo biotransformation in the uterine cavity to a different and nonuterine-retentive configuration and shaped whereby at the completion of said defined period of drug dispensing time, said drug dispensing device is facilely removed or spontaneously eliminated from the uterine cavity.

8. The drug dispensing device according to claim 7 wherein the drug is a member selected from the group consisting of progestational and estrogenic steroids and mixtures thereof.

9. A drug dispensing intrauterine device, shaped and adapted for insertion and positioning into the uterine cavity, with the device comprising in combination:
 a. a drug
 b. a delivery means adapted for insertion into the uterine cavity and for dispensing a therapeutically effective amount of drug to the uterine cavity over a defined period of time, and
 c. retention means for retaining the delivery means within the uterine cavity throughout the defined period of drug dispensing time, said retention means having an initial unit structural configuration shaped and adapted for insertion and positioning in the uterine cavity including means formed of a member selected from the group consisting of poly(vinyl alcohol), poly(ethylene oxide), poly(vinyl pyrrolidone), poly(acrylamide), poly(vinyl imidazole), poly(glycolic acid), poly(lactic acid), poly(peptide), poly(methacrylamide), copolymers of acrylamide and methacrylamide, water soluble hydrophilic polymers of uncross-linked hydroxyalkyl acrylates and methacrylates, and copolymers of poly(glycolic acid) and poly(lactic acid) that undergo biotransformation in the uterine cavity to a different and nonuterine-retentive configuration and shape whereby at the completion of said defined period of drug dispensing time, said drug dispensing device is facilely removed or spontaneously eliminated from the uterine cavity.

10. The device according to claim 9 wherein the drug is a member selected from the group consisting of progestational and estrogenic steroids and mixtures thereof.

11. A drug dispensing intrauterine device, shaped and adapted for insertion and placement in the uterine cavity, with the device comprising in combination:
 a. a drug
 b. a delivery means adapted for insertion into the uterine cavity for dispensing a therapeutically effective amount of drug to the uterine cavity over a defined period of time, and
 c. retention means for retaining the delivery means within the uterine cavity throughout the defined period of drug dispensing time, said retention means having an initial unit structural configuration shaped and adapted for insertion and placement in the uterine cavity including means formed of a polyester of the formula:

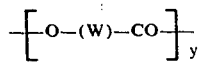

wherein W is a member selected from the group consisting of —CH₂— and

and Y has a value such that the molecular weight of the polymer is above 4,000, which polyester undergoes biotransformation in the uterine cavity to a different and nonuterine-retentive configuration and shape whereby at the completion of said defined period of drug dispensing time, said drug dispensing device is facilely removed or spontaneously eliminated from the uterine cavity.

12. The device for dispensing a drug according to claim 11 wherein the drug is a member selected from the group consisting of progestational and estrogenic steroids and mixtures thereof.

13. A drug dispensing device adapted and sized for insertion and placement in the uterine cavity comprising in combination:
  a. a drug
  b. a delivery means for supplying a therapeutically effective amount of drug to said cavity over a period of time, said delivery means comprising a body of erodible material formed of a member selected from the group consisting of poly(vinyl alcohol), poly(ethylene oxide), poly(vinyl pyrrolidone), poly(acrylamide), poly(vinyl imidazole), poly(glycolic acid), poly(lactic acid), poly(peptide), poly(methacrylamide), copolymers of acrylamide and methacrylamide, water soluble hydrophobic polymers of uncross-linked hydroxyalkyl acrylates and methacrylates, and copolymers of poly(glycolic acid) and poly(lactic acid) having drug dispersed therethrough which upon erosion releases drug at a controlled rate, and
  c. retention means for retaining said delivery means within the cavity throughout the period of time, with the retention means undergoing biotransformation by erosion in the cavity from a uterine retentive configuration to a nonuterine-retentive configuration whereby at the completion of the period of time, said device is facilely removed or spontaneously eliminated from said uterine cavity.

14. A drug dispensing device adapted, shaped and sized for insertion and placement in the uterine cavity comprising in combination:
  a. a drug
  b. a delivery means for supplying a therapeutically effective amount of drug to said cavity over a period of time, said delivery means comprising a body of erodible material formed of a member selected from the group consisting of protein, collagen, elastin, keratin, resilin and fibrin having drug dispersed therethrough which upon erosion releases drug at a controlled rate, and
  c. retention means for retaining said delivery means within the cavity throughout the period of time, with the retention means undergoing biotransformation by erosion in the cavity from a uterine retentive configuration to a nonuterine-retentive configuration whereby at the completion of the period of time, said device is facilely removed or spontaneously eliminated from said uterine cavity.

15. A drug dispensing device adapted for insertion into the uterine cavity comprising in combination:
  a. a drug
  b. a delivery means for supplying a therapeutically effective amount of drug to said cavity over a period of time, said delivery means comprising a body of erodible material formed of a member selected from the group consisting of a noncross-linked polysaccharide, algin, pectin, carrageenin, chitin, chondrotin sulfate, agar-agar, guar, locust bean gum, gum arabic, grum karaya, tragacanth and gum ghatti having drug disprsed therethrough which upon erosion releases drug at a controlled rate, and
  c. retention means for retaining said delivery means within the cavity throughout the period of time, with the retention means undergoing biotransformation by erosion in the cavity from a uterine retentive configuration to a nonuterine-retentive configuration whereby at the completion of the period of time, said device is facilely removed or spontaneously eliminated from said uterine cavity.

16. A drug dispensing device adapted for insertion into the uterine cavity comprising in combination:
  a. a drug
  b. a delivery means for supplying a therapeutically effective amount of drug to said cavity over a period of time, said delivery means comprising a body of erodible material formed of a member selected from the group consisting of starch, oxystarch, starch phosphate, carboxymethyl starch, sulfaethyl starch, aminoethyl starch, amidoethyl starch, starch esters, starch maleate, starch succinate, starch benzoate, starch acetate and mixtures of starch and gelatin having the drug dispersed therethrough which upon erosion releases drug at a controlled rate, and
  c. retention means for retaining said delivery means within the cavity throughout the period of time, with the retention means undergoing biotransformation by erosion in the from a froma uterine retentive configuration to a nonuterine-retentive configuration whereby at the completion of the period of time, said device is facilely removed or spontaneously eliminated from said uterine cavity.

17. A drug dispensing device adapted for insertion into the uterine cavity comprising in combination:
  a. a drug
  b. a delivery means for supplying a therapeutically effective amount of drug to said cavity over a period of time, said delivery means comprising a body of erodible material formed of a member selected from the group consisting of cellulose, hydroxyethylated cotton, carboxymethylated cotton and mixtures thereof having drug dispersed therethrough which upon erosion releases drug at a controlled rate, and
  c. retention means for retaining said delivery means within the cavity throughout the period of time, with the retention means undergoing biotransformation by erosion in the cavity from a uterine retentive configuration to a nonuterine-retentive configuration whereby at the completion of the period of time, said device is facilely removed or spontaneously eliminated from said uterine cavity.

18. A drug dispensing device adapted for insertion into the uterine cavity comprising in combination:
   a. a drug
   b. a delivery means for supplying a therapeutically effective amount of drug to said cavity over a period of time, said delivery means comprising a body of erodible material formed of a polyester of the general formula:

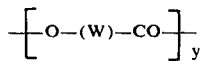

wherein W is a member selected from the group consisting of

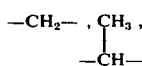

and mixtures thereof, and y has a value such that the molecular weight is above 4,000 and having drug dispersed therethrough which upon erosion releases drug at a controlled rate, and
   c. retention means for retaining said delivery means within the cavity throughout the period of time, with the retention means undergoing biotransformation by erosion in the cavity from a uterine retentive configuration to a nonuterine-retentive configuration whereby at the completion of the period of time, said device is facilely removed or spontaneously eliminated from said uterine cavity.

19. A drug dispensing device for insertion into a body cavity with the device comprising in combination:
   a. a drug
   b. a drug delivery means adapted for insertion into the cavity and for dispensing a therapeutically effective amount of drug to the cavity over a prolonged period of time, said delivery means comprising a wall enclosing said drug and permeable to the passage of said drug by diffusion and formed of a member selected from the group consisting of silicone rubbers, poly(dimethylsiloxane), ethylene vinylacetate copolymers, poly(isoprene), poly(isobutylene), poly(butadiene) and crosslinked hydrolyzed poly(vinylacetate), with passage of drug through the wall controlling the rate of release from the device, and
   c. retention means for retaining the delivery means within the cavity throughout the prolonged period of time, said retention means having an initial unit structure shape adapted for insertion and positioning in the cavity, with the retention means undergoing biotransformation in the cavity to a second structure noncavity-retentive structure whereby at the completion of the prolonged period of time, said device is facilely removed or spontaneously eliminated from the cavity.

20. A drug dispensing device for insertion into a mammalian body cavity with the device comprising in combination:
   a. a drug present in a dosage amount to produce a physiological or pharmacological effect,
   b. a drug delivery means adapted and sized for insertion into the cavity and for dispensing a therapeutically effective amount of drug to the cavity over a prolonged period of time, said delivery means comprising a wall enclosing said drug and permeable to the passage of said drug by diffusion, with passage of drug through the wall controlling the rate of release from the device, and
   c. retention means having a memory for retaining the delivery means within the cavity throughout the prolonged period of time, said retention means having an initial unit structural shape adapted for insertion, positioning and placement in the cavity, with the retention means and membory undergoing a gradual loss in the cavity to a different noncavity-retentive configuration whereby at the completion of the prolonged period of time, said device is facilely removed or spontaneously eliminated from the cavity.

21. The drug dispensing device according to claim 20 wherein the device dispenses a drug to a cavity selected from the group of cavities consisting of vagina and uterus.

22. A drug dispensing device adapted and sized for insertion into a mammalian body cavity comprising in combination:
   a. a drug present in a unit dosage amount for producing a local or systemic effect,
   b. a drug delivery means adapted for insertion into the cavity and for dispensing a therapeutically effective amount of drug to said cavity over a period of time, wherein said delivery means comprises an erodible material which upon erosion releases drug, and
   c. retention means having a memory for retaining the delivery means within the cavity throughout the prolonged period of time, said retention means having an initial unit structural shape adapted for insertion, positioning and placement in the cavity, with the retention means and memory undergoing a loss throughout the prolonged period of time in the cavity to a different noncavity-retentive configuration whereby at the completion of the prolonged period of time, said device is facilely removed or spontaneously eliminated from the cavity.

23. The drug dispensing device according to claim 22 wherein the device dispenses a drug to a cavity selected from the group consisting of the vagina and uterus.

* * * * *

UNITED STATES PATENT OFFICE
CERTIFICATE OF CORRECTION

Patent No. 3,971,367     Dated July 27, 1976

Inventor(s) Alejandro Zaffaroni

It is certified that error appears in the above-identified patent and that said Letters Patent are hereby corrected as shown below:

The term of this patent subsequent to August 12, 1992, has been disclaimed.

Signed and Sealed this

Twenty-eighth Day of September 1976

[SEAL]

Attest:

RUTH C. MASON
Attesting Officer

C. MARSHALL DANN
Commissioner of Patents and Trademarks